US009945802B2

(12) United States Patent
Fraikin et al.

(10) Patent No.: US 9,945,802 B2
(45) Date of Patent: *Apr. 17, 2018

(54) HIGH THROUGHPUT LABEL FREE NANOPARTICLE DETECTION AND SIZE ASSAY

(71) Applicant: THE REGENTS OF THE UNIVERSITY OF CALIFORNIA, Oakland, CA (US)

(72) Inventors: Jean-Luc Fraikin, Santa Barbara, CA (US); Andrew N. Cleland, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 531 days.

This patent is subject to a terminal disclaimer.

(21) Appl. No.: 14/528,551

(22) Filed: Oct. 30, 2014

(65) Prior Publication Data

US 2015/0059452 A1 Mar. 5, 2015

Related U.S. Application Data

(63) Continuation of application No. 13/362,220, filed on Jan. 31, 2012, now Pat. No. 8,901,914.
(Continued)

(51) Int. Cl.
*G01R 27/00* (2006.01)
*G01N 27/06* (2006.01)
(Continued)

(52) U.S. Cl.
CPC ......... *G01N 27/06* (2013.01); *G01N 15/1209* (2013.01); *G01N 33/18* (2013.01);
(Continued)

(58) Field of Classification Search
CPC ... G01N 2015/1062; G01N 2015/1486; G01R 31/12; G02B 5/3008
See application file for complete search history.

(56) References Cited

U.S. PATENT DOCUMENTS 2,656,508 A    10/1953  Coulter
4,019,134 A *   4/1977  Hogg ............... G01R 27/26
                                          324/71.1
(Continued)

OTHER PUBLICATIONS

Nohynek, G.J., et al., "Grey goo on the skin? Nanotechnology, cosmetic and sunscreen safety," Critical Reviews in Toxicology, vol. 37, pp. 251-277, Mar. 2007.
(Continued)

*Primary Examiner* — Tung X Nguyen
(74) *Attorney, Agent, or Firm* — Gates & Cooper LLP

(57) ABSTRACT

The present invention reports a novel microfluidic analyzer for the high-throughput, label-free measurement of particles suspended in a fluid. The present invention employs the resistive pulse technique (RPT) which affords very high electrical bandwidth for the device, which surpasses that of currently available systems and devices. Further, devices in accordance with the present invention are fabricated with very simple microfabrication technologies, making the present invention more cost efficient and easier to manufacture than currently available devices.

18 Claims, 3 Drawing Sheets

Related U.S. Application Data

(60) Provisional application No. 61/437,942, filed on Jan. 31, 2011.

(51) Int. Cl.
   G01N 15/12 (2006.01)
   G01N 33/18 (2006.01)
   G01N 15/00 (2006.01)
   G01N 15/10 (2006.01)

(52) U.S. Cl.
   CPC .......... G01N 2015/0038 (2013.01); G01N 2015/0092 (2013.01); G01N 2015/1062 (2013.01); G01N 2015/1087 (2013.01); G01N 2015/1236 (2013.01)

(56) References Cited

U.S. PATENT DOCUMENTS

| | | | |
|---|---|---|---|
| 6,426,615 B1 * | 7/2002 | Mehta ............... | G01N 15/0266 324/71.1 |
| 7,279,883 B2 | 10/2007 | Sohn et al. | |
| 8,184,290 B2 * | 5/2012 | Hertens ............. | G01F 1/667 356/335 |

OTHER PUBLICATIONS

Franzman, M.A., et al., "Solution-phase synthesis of SnSe nanocrystals for use in solar cells," Journal of the American Chemical Society, vol. 132, pp. 4060-4061, Mar. 2010.
Sugahara, K.N, et al., "Tissue-penetrating delivery of compounds and nanoparticles into tumors," Cancer Cell, vol. 16, pp. 510-520, Dec. 2009.
Michalet, X., et al., "Quantum Dots for Live Cells, in Vivo Imaging, and Diagnostics," Science, vol. 307, pp. 538-544, Jan. 2005.
Harisinghani, M.G., et al., "Noninvasive Detection of Clinically Occult Lymph-Node Metastases in Prostate Cancer," New England Journal of Medicine, vol. 348, pp. 2491-2499, Jun. 2003.
Vanwijk, M.I., et al., "Microparticles in cardiovascular diseases," Cardiovascular Research, vol. 59, pp. 277-287, Aug. 2003.
Valadi, H., et al., "Exosome-mediated transfer of mRNAs and microRNAs is a novel mechanism of genetic exchange between cells," Nature Cell Biology, vol. 9, pp. 654-659, Jun. 2007.
Simons, M., et al., "Exosomes—vesicular carriers for intercellular communication," Current Opinion in Cell Biology, vol. 21, pp. 575-581, Aug. 2009.
WHO, World Health Statistics 2010. WHO Press, 2010.
Nel, A. et al., "Toxic Potential of Materials at the Nanolevel," Science, vol. 311, No. 5761, pp. 622-627, Feb. 2006.
Maynard, A.D., et al., "Safe handling of nanotechnology," Nature, vol. 444, pp. 267-269, Nov. 2006.
Deblois, R.W., et al., "Counting and Sizing of Submicron Particles by the Resistive Pulse Technique," Review of Scientific Instruments, vol. 41, No. 7, pp. 909-916, Jul. 1970.
Kasianowicz, J.J., et al., "Characterization of individual polynucleotide molecules using a membrane channel," Proceedings of the National Academy of Sciences of the United States of America, vol. 93, No. 24, pp. 13770-13773, Nov. 1996.
Li, J., et al., "DNA molecules and configurations in a solid-state nanoporemicroscope," Nature Materials, vol. 2, pp. 611-615, Sep. 2003.
Uram, J.D., et al., "Label-Free Affinity Assays by Rapid Detection of Immune Complexes in Submicrometer Pores," Angewandte Chemie International Edition, vol. 45, No. 14, pp. 2281-2285, 2006.
Saleh, O.A., et al., "An Artificial Nanopore for Molecular Sensing," Nano Letters, vol. 3, pp. 37-38, Jan. 2003.
Sen, Y-H., et al., "Investigating the translocation of λ-DNA molecules through PDMS nanopores," Analytical and Bioanalytical Chemistry, vol. 394, pp. 437-446, May 2009.
Uram, J.D., et al., "Submicrometer Pore-Based Characterization and Quantification of Antibody-Virus Interactions," Small, vol. 2, No. 8-9, pp. 967-972, Aug. 2006.
Saleh, O.A, et al., "Quantitative sensing of nanoscale colloids using a microchip Coulter counter," Review of Scientific Instruments, vol. 72, pp. 4449-4451, Dec. 2001.
Berne, B.J, et al., Dynamic Light Scattering: With Applications to Chemistry, Biology, and Physics. New York: Wiley, 1976.
Teesalu, T., et al., "C-end rule peptides mediate neuropilin-1-dependent cell, vascular, and tissue penetration," Proceedings of the National Academy of Sciences, vol. 106, No. 38, pp. 16157-16162, Sep. 2009.
Wakita, T., et al., "Production of infectious hepatitis C virus in tissue culture from a cloned viral genome," Nature Medicine, vol. 11, pp. 791-796, Jul. 2005.
Davison, P.E. et al., "The Physical Properties of T7 Bacteriophage," Journal of Molecular Biology, vol. 5, pp. 635-642, Dec. 1962.
Ronto, G., et al., "Structure of Bacteriophage-T7—Small-Angle X-ray and Neutron-Scattering Study," Biophysical Journal, vol. 43, No. 3, pp. 309-314, Sep. 1983.
Serwer, P., "Buoyant Density Sedimentation of Macromolecules in Sodium Iothalamate Density Gradients," Journal of Molecular Biology, vol. 92, No. 3, pp. 433-448, 1975.
Stroud, R.M, et al., "Assembly of Bacteriophage T7—Dimensions of the Bacteriophage and its Capsids," Biophysical Journal, vol. 36, No. 3, pp. 743-757, Dec. 1981.
Berg T., et al., "Prediction of Treatment Outcome in Patients With Chronic Hepatitis C: Significance of Baseline Parameters and Viral Dynamics During Therapy," Hepatology, vol. 37, pp. 600-609, Mar. 2003.
Caby, M-P, et al., "Exosomal-like vesicles are present in human blood plasma," International Immunology, vol. 17, No. 7, pp. 879-887, 2005.
Kiser, M.A., et al., "Titanium Nanomaterial Removal and Release from Wastewater Treatment Plants," Environmental Science & Technology, vol. 43, pp. 6757-6763, Sep. 2009.
Gottschalk, F., et al., "Modeled Environmental Concentrations of Engineered Nanomaterials (TiO2, ZnO, Ag, CNT, Fullerenes) for Different Regions," Environmental Science & Technology, vol. 43, pp. 9216-9222, Dec. 2009.
Duffy D., et al., "Rapid Prototyping of Microfluidic Systems in Poly(dimethylsiloxane)," Analytical Chemistry, vol. 70, No. 23, pp. 4974-4984, Dec. 1998.
Fraikin, J.-L., et al., "Probing the Debye Layer: Capacitance and Potential of Zero Charge Measured using a Debye-Layer Transistor," Phys. Rev. Lett., vol. 102, pp. 156601-1-156601-4, Apr. 2009.
Wood, D.K., et al., "High-bandwidth radio frequency Coulter counter," Applied Physics Letters, vol. 87, No. 18, p. 184106-1-184106-3, 2005.
Wood, D.K., et al., "Microfabricated high-throughput electronic particle detector," Review of Scientific Instruments, vol. 78, No. 10, p. 104301-1-104301-6, 2007.
Wood, D.K., et al., "A feasible approach to all-electronic digital labeling and readout for cell identification," Lab on a Chip, vol. 7, No. 4, pp. 469-474, 2007.
Deblois, R.W, et al., Electrokinetic Measurements with Sub-micron Particles and Pores by the Resistive Pulse Technique, Journal of Colloid and Interface Science, vol. 61, pp. 323-335, Sep. 1977.
Sridhar, M., et al., Experimental characterization of a metal-oxide-semiconductor field-effect transistor-based Coulter counter, Journal of Applied Physics, vol. 103, pp. 104701-1-104701-10, 2008.
Leif, R.C, et al., "Electronic Cell-Volume Analysis by Use of the AMAC I Transducer," Clinical Chemistry, vol. 19, No. 8, 1973.
Leif, R.C, et al., "The Automated Multiparameter Analyzer for Cells (AMAC) IIA, A True Bridge Circuit Coulter-Type Electronic Cell Volume Transducer", Journal of Histochemistry and Cytochemistry, vol. 27, No. 1, pp. 225-233, 1979.
Thomas, R.A., et al., "Computer-Based Electronic Cell Volume Analysis with the AMAC II Transducer", Journal of Histochemistry and Cytochemistry, vol. 22, No. 7, pp. 626-641, 1974.
Kubitschek, H.E., Counting and Sizing Micro-organisms with the Coulter Counter, vol. 1, ch. XXVII, pp. 593-610. Academic Press, 1969.

(56) References Cited

OTHER PUBLICATIONS

Cressey, D., "Tiny traits cause big headaches", Macmillan Publishers Limited, 2010.
Bard, A.J., Electrochemical Methods Fundamentals and Applications. Wiley, Second Ed., 1980.

* cited by examiner

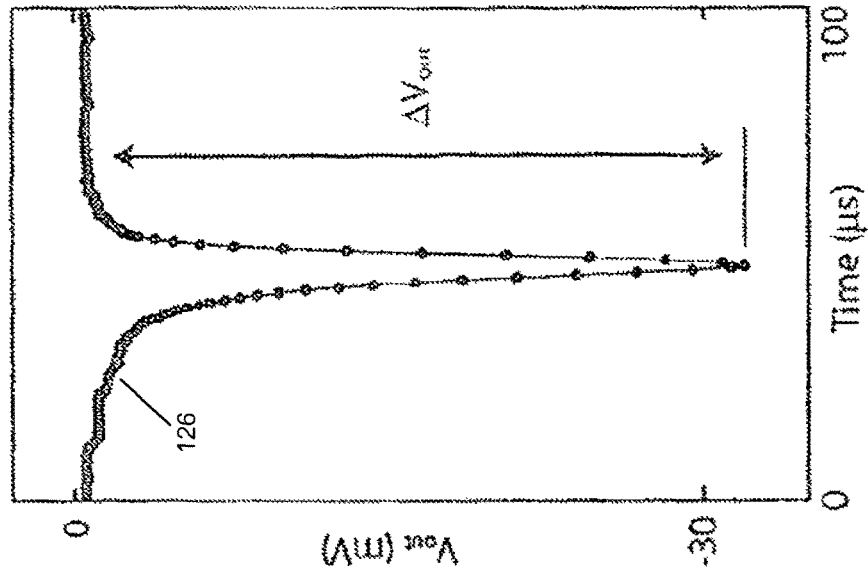
FIG. 1C
FIG. 1B
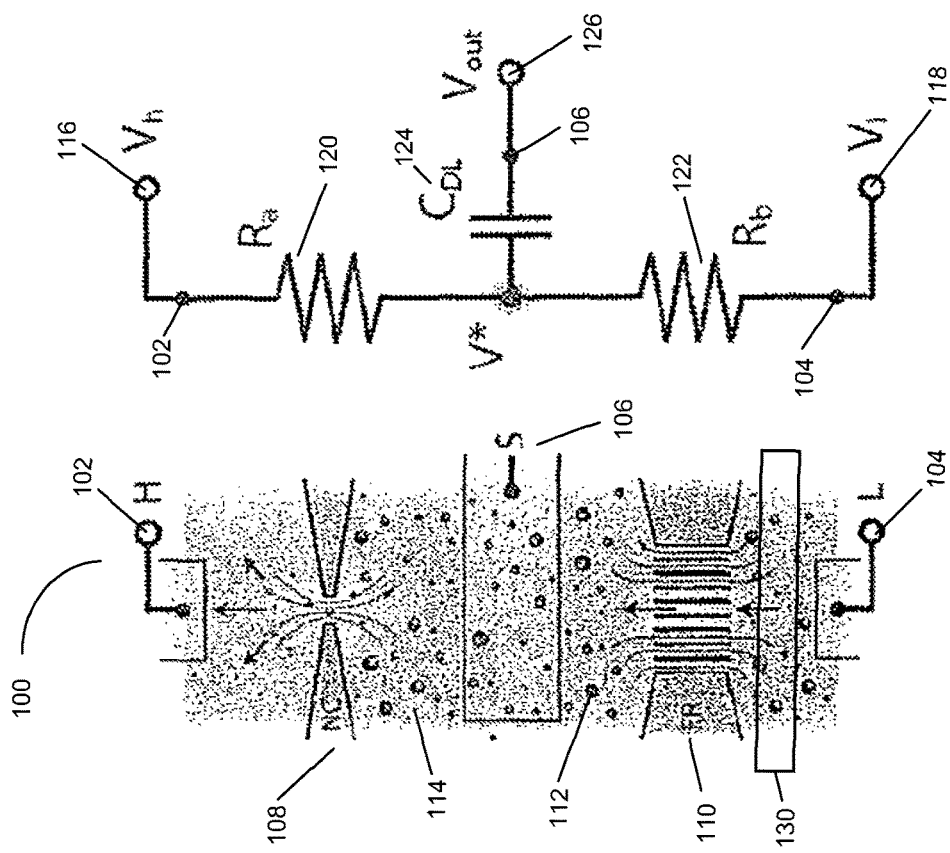
FIG. 1A

HIGH THROUGHPUT LABEL FREE NANOPARTICLE DETECTION AND SIZE ASSAY

CROSS-REFERENCE TO RELATED APPLICATIONS

This application is a continuation under 35 U.S.C. Section 120 of commonly-assigned:

U.S. Utility patent application Ser. No. 13/362,220, filed on Jan. 31, 2012, by Jean-Luc Fraikin and Andrew N. Cleland, entitled "HIGH THROUGHPUT LABEL FREE NANOPARTICLE DETECTION AND SIZE ASSAY," now U.S. Pat. No. 8,901,914, issued Dec. 2, 2014, which application claims the benefit under 35 U.S.C. Section 119(e) of commonly-assigned:

U.S. Provisional Patent Application Ser. No. 61/437,942, filed on Jan. 31, 2011, by Jean-Luc Fraikin and Andrew N. Cleland, entitled "HIGH THROUGHPUT LABEL FREE NANOPARTICLE DETECTION AND SIZE ASSAY,", both of which applications are incorporated by reference herein.

STATEMENT REGARDING FEDERALLY SPONSORED RESEARCH AND DEVELOPMENT

This invention was made with Government support under Grant/Contract No. U01 HL080718 awarded by the National Institutes of Health. The Government has certain rights in this invention.

BACKGROUND OF THE INVENTION

1. Field of the Invention

The present invention relates generally to microfluidics, and specifically to a high-throughput, label-free measurement of nano- and micro-particles suspended in a fluid.

2. Description of the Related Art

Counting and measuring particles suspended in a conducting fluid has been taking place in biomedical applications for almost fifty years. A resistive pulse technique has been used to size and count microparticles suspended in conducting fluid since Coulter first patented such in U.S. Pat. No. 2,656,508, which is herein incorporated by reference. Many incremental improvements to this original concept have been used since, and include modifications of the approach in order to achieve nanoparticle (dia. <1 micrometer) detection and measurement.

Of these improvements, two approaches seem to have provided promising results. The first, set forth in U.S. Pat. No. 7,279,883, which is incorporated by reference herein, uses a four-wire sensing technique, which is inherently limited in bandwidth by the current-sensing capabilities of the electronics.

The second approach, described in Leif et al. (Clin. Chem. 8:853 (1973); J. Histo. Chem. 22:626 (1974), J. Histo. Chem. 27:225 (1979)), which is incorporated by reference herein, describe the use of a fluidic voltage divider for the detection of microparticles (dia. >1 micrometer) and cells. These instruments are not nanofabricated, and are instead very complex, three-dimensional large structures which are costly to fabricate and operate.

It can be seen, then, that there is a need in the art for a non-bandwidth-limited system to measure and detect micro- and nanoparticles in fluid. It can also be seen that there is a need in the art for systems and devices that can measure and detect micro- and nanoparticles, systems and devices that are easier to fabricate and operate than those currently available.

SUMMARY OF THE INVENTION

The present invention describes a novel microfluidic analyzer for the high-throughput, label-free measurement of micro- and nanoparticles suspended in a fluid.

A device in accordance with one or more embodiments of the present invention comprises a microfluidic channel, which directs the flow of analyte through the electrical sensor and is designed to maximize the measurement bandwidth of the device; and a sensor, which comprises two or more voltage-bias electrodes and one or more readout electrode(s) embedded in the microchannel.

The present invention employs the resistive pulse technique (RPT) implemented in a manner that affords very high electrical bandwidth for the device, which surpasses that of currently available systems and devices. Further, devices in accordance with the present invention are fabricated with very simple microfabrication technologies, making the present invention more cost efficient and easier to manufacture than currently available devices.

An apparatus for detecting particles in a fluid in accordance with one or more embodiments of the present invention comprises a first electrode, a sensing electrode, a fluid resistor between the first electrode and the sensing electrode, a second electrode, and a constriction between the sensing electrode and the second electrode, wherein a bias voltage is applied between the first electrode and the second electrode to create a current through the fluid, such that a size and a number of a particle is sensed by a change in voltage sensed at the sensing electrode.

Such an apparatus further optionally comprises a filter element such that the particles are sensed by the apparatus and undesired particles are blocked by the filter element from being sensed by the apparatus, a bandwidth of the apparatus being greater than 100 kHz, the fluid resistor and the constriction comprise a voltage divider in the apparatus, the sensing electrode being fabricated using lithographic techniques, the bias voltage being a constant voltage, the apparatus sensing different sizes of particles in the fluid, a plurality of constrictions, and an integrated filter element.

A method of detecting particles in a fluid in accordance with one or more embodiments of the present invention comprises applying a bias voltage between a first electrode and a second electrode, filtering the fluid prior to entering any smaller constrictions, restricting the fluid in a constriction between the first electrode and the second electrode, and sensing a change in voltage at a point between the constriction and the second electrode, wherein the change in voltage is proportional to a volume filling fraction of a particle in the constriction.

Such a method further optionally includes a bandwidth of the apparatus being greater than 100 kHz, creating a voltage divider in the apparatus using the constriction, the sensing electrode being fabricated using lithographic techniques, the bias voltage being a constant voltage, sensing different sizes of particles in the fluid, and constricting the fluid in a plurality of constrictions.

BRIEF DESCRIPTION OF THE DRAWINGS

Referring now to the drawings in which like reference numbers represent corresponding parts throughout:

FIGS. 1A-1C illustrate device schematics, detector response, and operation of one or more embodiments of the present invention.

DETAILED DESCRIPTION OF THE INVENTION

Figure 1D:
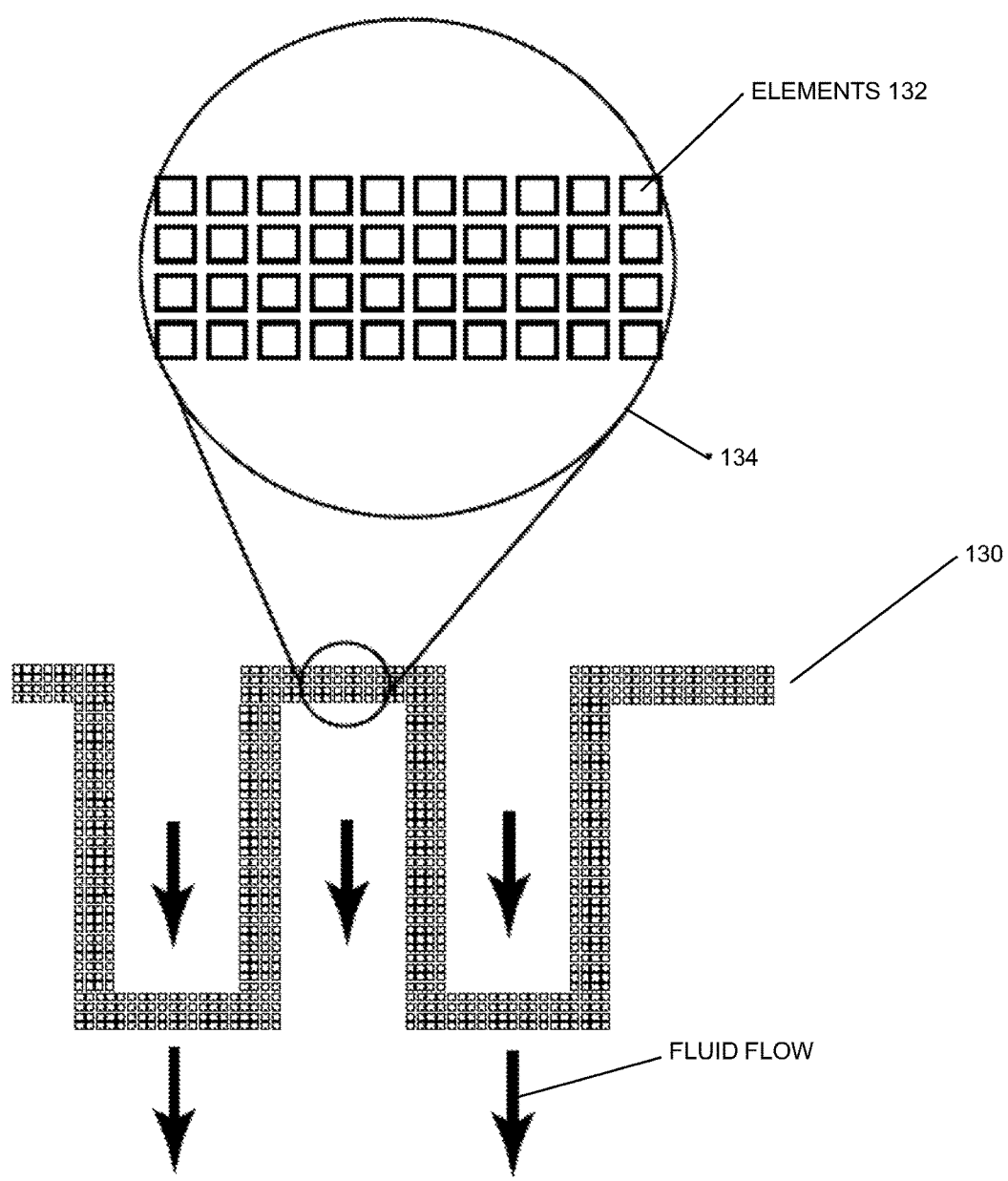
FIG. 1D illustrates a filtration system in accordance with one or more embodiments of the present invention.

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

FIGS. 1A-1C illustrate device schematics, detector response, and operation of an embodiment of the present invention.

FIG. 1A illustrates system 100, with electrode H 102, electrode L 104, and sensing electrode 106. Between electrode H 102 and sensing electrode 106 is a constriction 108, which can be fabricated with cross-sectional dimensions ranging from nanometers to micrometers, and between sensing electrode 106 and electrode L 104 is a fluid resistor 110. Particles 112 suspended in a pressure driven solution 114, typically a saline solution, are driven along the channel between electrode H 102 and electrode L 104 through the constriction 108, and possibly although not necessarily through the fluid resistor 110. Electrodes H 102 and L 104 are voltage-biased, and changes in the electrical potential of the fluid 114 adjacent to the constriction 108 are detected by the sensing electrode 106. The passage of particles through the constriction 108 changes the effective electrical resistance of the fluid 114 contained in the constriction 108, which combined with the voltage bias provided by electrodes H 102 and L 104, changes the electrical potential of the sensing electrode 106. The optional passage of particles through the fluid resistor 110 does not appreciably change the corresponding fluidic resistance, so that no corresponding signal is generated in sensing electrode 106, in contrast to passage of the particles through the constriction 108. The sensing electrode is typically, though not necessarily, lithographically manufactured. Although shown in the center between electrodes H 102 and L 104, sensing electrode 106 can be placed anywhere in the region between electrodes H 102 and L 104, so long as the changes in the effective electrical resistance of the fluid 114 contained in the constriction 108 can be properly and/or accurately detected by sensing electrode 106. Further, fluid resistor 110 and constriction 108 can be placed anywhere in the system 100.

FIG. 1B illustrates an electrical equivalent circuit to the system 100 shown in FIG. 1A. Typically, a constant bias voltage Vh 116 is applied to electrode H 102, and a constant bias voltage Vl 118 is applied to electrode L 104, although varying bias voltages can be applied if desired. The application of a bias voltage difference between the electrodes 102 and 104 causes an ionic current to flow in the fluid 114. Resistors Ra 120 and Rb 122 represent the electrical resistance of the fluid in the constriction 108 and the fluidic resistor 110 respectively. The sensing electrode 106 is capacitively-coupled to the fluid through the electric double layer capacitance Cdl 124. The circuit elements Ra 120, Rb 122, and Cdl 124 are measureable directly. The output voltage Vout 126 is measured as the output from sensing electrode 106.

The ionic current between electrodes 102 and 104 creates voltage drops across the constriction 108 in the fluid channel and the fluid resistor 110 which typically presents an approximately equal fluidic electrical resistance but has a larger volume. The sensing electrode 106 is embedded in the fluid between the constriction 108 and the fluid resistor 110. When a particle enters the constriction 108, it alters the ionic electrical current and, because of the voltage division between the two fluidic resistances, changes the electrical potential of the sensing electrode 106. The time-varying nature of the particle passage through the constriction makes the electrical potential at the sensing electrode 106 time-varying as well, which allows this signal to be electrically coupled through the electrical double layer capacitance Cdl 124. The signal 126 can be amplified with an operational amplifier or other type of amplifier as desired to properly measure the output voltage 126.

The present invention optionally includes filtration systems 130 manufactured in a size commensurate with the constriction 108 to avoid clogging by large particles and to allow for longer uninterrupted run times. The filtration systems can be scaled in size and can be manufactured using existing fabrication techniques currently used elsewhere in the device. Although shown near fluidic resistor 110, filtration system 130 can be placed anywhere in the system 100 without departing from the scope of the present invention.

Further, the system 100 can be optimized in the channel design to allow automation of the channel filling process. Such optimization can include specialized purpose-built electronics, possibly in miniaturized electronic formats, and microfluidic features that can be manufactured using the techniques shown in the present invention.

The system 100 of the present invention can also comprise a sorting mechanism, which can be a part of fluidic resistor 110 or optional filtration system 130, or a separate sorting mechanism if desired, so that particles meeting selection criteria may be separated from a fluid 114 mixture.

The present invention can be manufactured in an array geometry, allowing scaling to large numbers of parallel detection channels (e.g., parallel constrictions 108 and/or parallel fluid resistors 110 and/or parallel filtration systems) which can be employed in the present invention to increase the range of particle sizes that can be detected with the sensor electrode 106 (or parallel sensor electrodes 106). Such approaches can also be used to develop size-based antibody assays, and to size and measure the concentration of particles in solution, and to determine other properties of the particles, such as electrical charge. Related art approaches currently do not provide the size resolution and direct measurement of particle concentration as is possible through the present invention.

FIG. 1C illustrates a measurement of Vout 126 as a function of time as a single particle of nominal diameter 117 nm traverses the constriction 108, showing excellent time resolution and signal-to-noise ratio. The peak voltage change Δ Vout is proportional to the bias voltage difference (Vh 116-Vl 118) and to the volume filling fraction of the particle in the constriction 108.

FIG. 1D illustrates a filtration system in accordance with one or more embodiments of the present invention.

Filtration system 130 is shown, with individual elements 132 of the optional filter shown in detail section 134. Other optional filtration systems are possible within the scope of the present invention as needed for a specific application;

some applications may not need or desire any filtration system 130 within system 100.

Analyzer Features

The analyzer of the present invention has several advantages over analyzers of the related art. First, the analyzer of the present invention is fabricated using a completely scalable process, allowing parallel lithographic or other manufacture of large numbers of identical or similar devices. The fluidic components of the device can be made of molded poly-(dimethylsiloxane) (PDMS), using well-established molding or nano-imprint lithography. The sensing electrode can be made of gold, patterned on a glass substrate using single-layer optical lithography. Other materials can be used without departing from the scope of the present invention. The scalable fabrication process of the present invention allows for very low-cost fabrication of analyzer chips, to the point where the chip is disposable.

Another characteristic of the device of the present invention is a high-throughput detection capability, which results from the type of signal transduction. Rather than cumbersome four-wire techniques, or large devices that are complex to build and operate, the fluidic network of the present invention acts as a balanced voltage divider, so a voltage output signal is produced using a voltage bias.

The analyzer of the present invention also has excellent size resolution. Rather than particle size distributions being extracted from bulk measurements such as dynamic light scattering or disk centrifugation, which methods are inherently ensemble-averaging and limited in size resolution and unable to detect rare particles, the present invention has better size and particle counting resolution through the use of the constriction and simple electronic design, with the further ability to perform sophisticated population analysis using the individual-particle detection capability.

Related art approaches are also inherently limited in bandwidth to audio frequencies (less than a few kilohertz) by the requirement of current-sourcing, or current-sensing electronics. These limitations prevent the adoption of RPT methods as practical analytic tools for high-throughput detection of particles smaller than approximately 1 micrometer (um) in diameter. The present invention allows for significantly higher detection bandwidth (approximately 1000 times greater at 650 kHz bandwidths) allowing for a much greater throughput, sufficient to detect particles with diameter <100 nm at rates exceeding 500,000 particles per second, so that large sample numbers and significant population statistics can be achieved in much shorter sampling times. The present invention is capable of bandwidths greater than 100 kHz, and has been experimentally shown at 650 kHz, which is far in excess of the related art techniques.

Other voltage divider techniques of the related art are very complex, three-dimensional large structures, which limit the commercial use and application of such devices. The simple, scalable fabrication techniques of the present invention reduce costs and make such devices more available to a wider application in industry and scientific research.

Although individual particles can be studied by electron microscopy, this approach is costly, slow, and not practical for collecting large population statistics. Because the present invention measures each particle individually as it passes through the sensing volume, it has inherently finer size resolution than bulk measurement techniques and can detect rare particles. The present invention has experimentally distinguished subcomponents of a polydisperse particle mixture with diameters larger than about 30-40 nm, a task that dynamic light scattering, the most commonly used technique for sizing nanoparticles below 1 um, cannot accomplish.

The present invention allows for analyzers to be used in several applications, e.g., size distribution analysis and concentration measurements of synthetic and biological particle mixtures, particle surface chemistry analysis using a change in size resulting from particle agglomeration, a change in size caused directly by molecular binding of a specific reporter molecule to the particles, biomolecular detection using a change in size resulting from particle agglomeration, a change in size caused directly by molecular binding of the target to the particles, virus or other particle-targeting antibody development, and analysis of other particle properties that lead to differences in the change in effective resistance of the constriction caused by the particles, such as surface charge.

Process Chart

Figure 2:
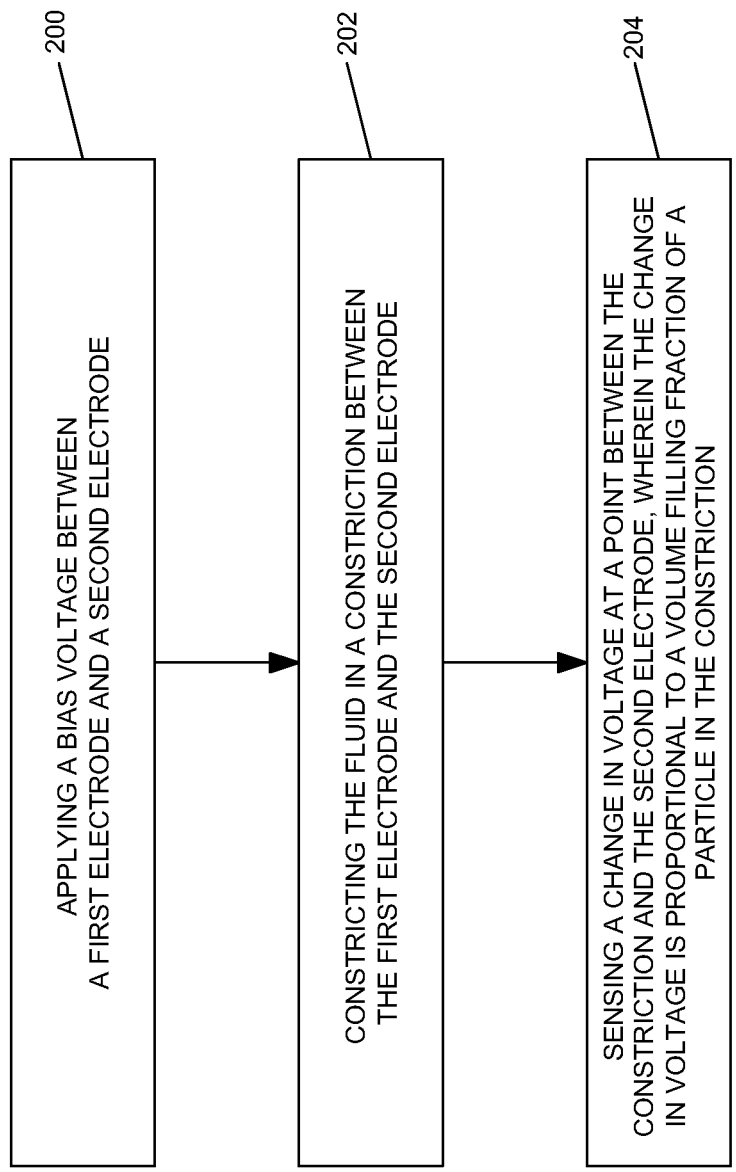
FIG. 2 illustrates a process chart in accordance with one or more embodiments of the present invention.

FIG. 2 illustrates a process chart in accordance with one or more embodiments of the present invention.

Box 200 illustrates applying a bias voltage between a first electrode and a second electrode.

Box 202 illustrates constricting the fluid in a constriction between the first electrode and the second electrode.

Box 204 illustrates sensing a change in voltage at a point between the constriction and the second electrode, wherein the change in voltage is proportional to a volume filling fraction of a particle in the constriction.

Device Applications

Although the present invention is described in terms of a device, it is also contemplated within the scope of the present invention that the device of the present invention is used in conjunction with other devices in various applications. For example, and not by way of limitation, the device of the present invention can be used to measure particles and/or nanoparticles in a variety of applications, such as blood plasma sampling devices, measuring particles and/or nanoparticles in protein agglomeration, measuring particle distributions in products such as cosmetics, industrial products, ink, paint, personal care products, etc. Such applications of the present invention can be used, for example, for quality control of products and chemical mechanical processes, as a feedback mechanism for industrial machinery, as a measuring device for real-time or delayed sampling, or other applications where particle measurement, sampling, and volume filling fractions are desired or required.

CONCLUSION

This concludes the description of the preferred embodiment of the present invention.

In conclusion, an apparatus for detecting particles in a fluid in accordance with one or more embodiments of the present invention comprises a first electrode, a sensing electrode, a fluid resistor between the first electrode and the sensing electrode, a second electrode, and a constriction between the sensing electrode and the second electrode, wherein a bias voltage is applied between the first electrode and the second electrode to create a current through the fluid, such that a size and a number of a particle is sensed by a change in voltage sensed at the sensing electrode.

Such an apparatus further optionally comprises a filter element such that the particles are sensed by the apparatus and undesired particles are blocked by the filter element from being sensed by the apparatus, a bandwidth of the apparatus being greater than 100 kHz, the fluid resistor and the constriction comprise a voltage divider in the apparatus, the sensing electrode being fabricated using lithographic techniques, the bias voltage being a constant voltage, the apparatus sensing different sizes of particles in the fluid, a plurality of constrictions, and an integrated filter element.

A method of detecting particles in a fluid in accordance with one or more embodiments of the present invention comprises applying a bias voltage between a first electrode and a second electrode, filtering the fluid prior to entering any smaller constrictions, restricting the fluid in a constriction between the first electrode and the second electrode, and sensing a change in voltage at a point between the constriction and the second electrode, wherein the change in voltage is proportional to a volume filling fraction of a particle in the constriction.

Such a method further optionally includes a bandwidth of the apparatus being greater than 100 kHz, creating a voltage divider in the apparatus using the constriction, the sensing electrode being fabricated using lithographic techniques, the bias voltage being a constant voltage, sensing different sizes of particles in the fluid, and constricting the fluid in a plurality of constrictions.

The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto and the full range of equivalents to the claims appended hereto.

What is claimed is:

1. An apparatus for detecting particles in a fluid, comprising:
   a first electrode;
   a sensing electrode;
   a fluid resistor positioned between the first electrode and the sensing electrode;
   a second electrode; and
   a constriction positioned between the sensing electrode and the second electrode;
   wherein a bias voltage is applied between the first electrode and the second electrode to create a current through the fluid, such that one or more properties for particles in the fluid are sensed by a change in voltage sensed at the sensing electrode.

2. The apparatus of claim 1, wherein particles of different sizes are distinguished by the change in voltage sensed at any of the electrodes.

3. The apparatus of claim 1, wherein particles which differ in properties other than size are distinguished by the change in voltage sensed at any of the electrodes.

4. The apparatus of claim 1, wherein the properties comprise electrical properties of the particles.

5. The apparatus of claim 1, wherein changes in the apparatus are detected by the change in voltage sensed at any of the electrodes.

6. The apparatus of claim 1, wherein a change in particle size resulting from particle agglomeration due to a presence of specific particle surface chemistry is detected by the change in the voltage sensed at any of the electrodes and thereby used as a method for the analysis of particle surface chemistry.

7. The apparatus of claim 1, wherein a change in particle size resulting from binding of molecules to the particles is detected by the change in the voltage sensed at any of the electrodes and thereby used as a method for analysis of particle surface chemistry.

8. The apparatus of claim 1, wherein the change in the voltage sensed at any of the electrodes is used to detect a presence of specific molecules in the fluid, such that a change in particle size resulting from particle agglomeration due to the presence of the specific molecules in the fluid is detected by this change in the voltage.

9. The apparatus of claim 1, wherein the change in the voltage sensed at any of the electrodes is used to detect a presence of specific molecules in the fluid, such that a change in particle size resulting from binding of the specific molecules to the particles is detected by this change in the voltage.

10. The apparatus of claim 1, wherein a distribution of particle sizes resulting from agglomeration is detected by the change in the voltage sensed at any of the electrodes and is subsequently analyzed, thereby giving information on an amount and/or concentration of specific molecules present in the fluid.

11. The apparatus of claim 1, wherein a distribution of particle sizes resulting from binding of molecules is detected by the change in the voltage sensed at any of the electrodes and is subsequently analyzed, thereby giving information on an amount and/or concentration of specific molecules present in the fluid.

12. The apparatus of claim 1, wherein the change in the voltage indicates a time of residence of a particle in the constriction.

13. The apparatus of claim 1, wherein the change in the voltage indicates a volume flow rate of the fluid through the constriction.

14. The apparatus of claim 13, wherein the volume flow rate indicates a concentration of one or more of the particles in the fluid.

15. The apparatus of claim 1, further comprising one or more electrodes in contact with the fluid on one or more sides of the fluid resistor and the constriction.

16. The apparatus of claim 1, wherein the design of a channel in contact with one or more of the electrodes is optimized to allow automation of a channel filling process in such a way that a position of one or more of the electrodes permits detection of the channel filling process.

17. The apparatus of claim 1, wherein one or more of the electrodes permits measurement of a conductivity of a current path.

18. The apparatus of claim 1, wherein the fluid resistor presents an approximately equal fluidic electrical resistance but has a larger volume as compared to the constriction.

* * * * *